United States Patent
Knight et al.

(10) Patent No.: US 7,842,932 B2
(45) Date of Patent: Nov. 30, 2010

(54) ULTRAVIOLET RADIATION LIGHT EMITTING DIODE DEVICE

(75) Inventors: Douglas G. Knight, London (CA); Jim Fraser, London (CA); Michael Sasges, Victoria (CA)

(73) Assignee: Trojan Technologies (CA)

( * ) Notice: Subject to any disclaimer, the term of this patent is extended or adjusted under 35 U.S.C. 154(b) by 232 days.

(21) Appl. No.: 12/131,485

(22) Filed: Jun. 2, 2008

(65) Prior Publication Data

US 2009/0026385 A1 Jan. 29, 2009

Related U.S. Application Data

(60) Provisional application No. 60/924,849, filed on Jun. 1, 2007.

(51) Int. Cl.
*A61L 2/10* (2006.01)
*C02F 1/32* (2006.01)

(52) U.S. Cl. ............... 250/435; 250/494.1; 250/504 R; 422/22; 422/24

(58) Field of Classification Search ........... 250/429, 250/432 R, 436, 437, 438, 493.1, 494.1, 504 R, 250/428, 433, 435, 504 H; 422/1, 20, 21, 422/22, 23, 24, 28; 210/748.01, 748.1, 748.11, 210/748.12; 257/79, 81, 88, 98, 99, 100
See application file for complete search history.

(56) References Cited

U.S. PATENT DOCUMENTS 5,874,747 A 2/1999 Redwing et al.
5,900,212 A * 5/1999 Maiden et al. ............... 422/24
7,125,526 B2 * 10/2006 Sheehan ................... 422/186.3
7,671,346 B2 * 3/2010 Siegel ..................... 250/492.1
2005/0023482 A1 * 2/2005 Schulz .................... 250/432 R
2006/0131246 A1 * 6/2006 Ehlers ........................ 210/748
2006/0163126 A1 7/2006 Maiden
2006/0267043 A1 11/2006 Emerson et al.
2007/0090272 A1 * 4/2007 Wang ......................... 250/205
2008/0116054 A1 * 5/2008 Leach et al. ............. 204/157.3
2008/0251806 A1 * 10/2008 Erchak ........................ 257/98
2008/0265179 A1 * 10/2008 Havens et al. ............ 250/492.1

OTHER PUBLICATIONS

International Search Report for International Application No. PCT/CA2008/001036.

* cited by examiner

*Primary Examiner*—Jack I Berman
*Assistant Examiner*—Nicole Ippolito Rausch
(74) *Attorney, Agent, or Firm*—Katten Muchin Rosenman LLP

(57) ABSTRACT

There is disclosed an ultraviolet radiation device. The device comprises a base portion, a plurality of semiconductor structures connected to the base portion and an ultraviolet radiation transparent element connected to the plurality of semiconductor structures. Preferably: (i) the at least one light emitting diode is in direct contact with the ultraviolet radiation transparent element, or (ii) there is a spacing between the at least one light emitting diode and the ultraviolet radiation transparent element, the spacing being substantially completely free of air. There is also disclosed a fluid treatment system incorporating the ultraviolet radiation device.

53 Claims, 6 Drawing Sheets

ULTRAVIOLET RADIATION LIGHT EMITTING DIODE DEVICE

CROSS-REFERENCE TO RELATED APPLICATION

The present application claims the benefit under 35 U.S.C. §119(e) of provisional patent application Ser. No. 60/924,849, filed Jun. 1, 2007, the contents of which are hereby incorporated by reference.

BACKGROUND OF THE INVENTION

1. Field of the Invention

In one of its aspects, the present invention relates to an ultraviolet radiation light emitting diode (LED) device. In another of its aspects, the present invention relates to a fluid treatment system comprising an ultraviolet radiation LED device.

2. Description of the Prior Art

Fluid treatment systems are known generally in the art.

For example, U.S. Pat. Nos. 4,482,809, 4,872,980, 5,006,244, 5,418,370, 5,539,210 and Re:36,896 (all in the name of Maarschalkerweerd and all assigned to the assignee of the present invention) all describe gravity fed fluid treatment systems which employ ultraviolet (UV) radiation.

Generally, such prior fluid treatment systems employ an ultraviolet radiation lamp to emit radiation of a particular wavelength or range of wavelengths (usually between 185 and 400 μm) to effect bacterial kill or other treatment of the fluid being treated. Conventional ultraviolet radiation lamps are so-called "low pressure" mercury lamps and "medium pressure" lamps.

The art in low pressure mercury lamps has evolved with the development of the so-called Low Pressure, High Output (LPHO) and amalgam UV radiation lamps. These lamps have found widespread use in UV radiation water treatment systems, particularly those used for treatment of municipal drinking water and wastewater. As used herein, the term "low pressure" UV radiation lamp is intended to encompass conventional UV radiation lamps, LPHO UV radiation lamps and amalgam UV radiation lamps.

In recent years, an interest has evolved in light emitting diodes (LEDs) as an alternate source of ultraviolet radiation.

With respect to UV LEDs, the prior art approaches have revolved around grouping individual LEDs into lighting systems that would be used as a light source.

For example, International Publication Number WO05/031881 [Jensen] teaches a tubular LED light source that involves substitution of a cylindrical group of LEDs for a standard cylindrical lamp in a lamp sleeve in conventional fluorescent lighting.

A similar design for the UV LED light source in a portable water disinfection system is taught by International Publication Number WO04/028290 [Maiden].

United States Patent Application Publication US2005/0000913 [Betterly] teaches a fluid treatment system in which this scheme is inverted—i.e., a scheme wherein an outside cylinder of LEDs directs UV light inwards toward a transparent pipe where the water to be disinfected flows.

The disadvantage of the approaches taught by Jensen, Maiden and Betterly is the difficulty in achieving heat extraction from the individual LEDs arranged in their respective geometries. A further disadvantage of the approaches taught by Jensen, Maiden and Betterly is the low UV power densities possible with individual light sources. The low power density possible in a practical disinfection device such as that of Maiden results in low possible flow rates for disinfecting water. That is why this system is a small personal use system. An alternate reactor geometry of Betterly has a rectangular array of LEDs that are shown protruding from a rectangular weir (see FIG. 4 of Betterly)—this makes cleaning very difficult once fouling occurs in the disinfection reactor. FIG. 4 of Betterly is based on a standard epoxy encapsulant that would surround the LED chip giving the illustrated bullet-shaped profile. Epoxy encapsulation for a UV LED is not feasible due to the fact that a conventional epoxy encapsulant is susceptible to degradation over time upon prolonged exposure to UV radiation.

International Publication Number WO 05/31881 [Scholl] teaches a disinfecting lamp using semiconductors with AlGaN alloys. No practical demonstration of these lamps is presented. Scholl teaches that the current effectiveness of AlGaN LEDs "can be improved from the current 20% to 40%". Scholl further teaches that the power density of a hypothetical LED of 1 W UV power output and 40% effectiveness with a 1 mm$^2$ area is 40 W/cm$^2$. This would compare favorably to standard mercury lamps with power densities of 0.04-1.5 W/cm$^2$. However, there are two problems with this statement. First, the power density would only be 40 W/cm$^2$ directly above the LED chip. Over the entire area of the device of a sample area of 1 cm$^2$, the power density would drop to an average of 0.4 W/cm$^2$. Second, the state of the art UV for output in UV LEDs emitting in the germicidal wavelength region of ~240-280 run is only ~1 mW at 280 nm (see J. P. Zhang et al., "AlGaN-based 280 nm light-emitting diodes with continuous-wave power exceeding 1 mW at 25 mA", Applied Physics Letters 85, p. 5532-5534, 2004).

Thus, the state of the art average power density for a UV LED is therefore ~1 mW/cm$^2$, which is much less than that of mercury lamps. In Zhang et al, the efficiency of the state of the art 280 nm LED is only 0.85% versus the 20-40% mentioned above.

Thus, despite the purported advances made in the art, there is an ongoing need for an actual UV LED that can be used as an efficient and effective disinfection light source.

SUMMARY OF THE INVENTION

It is an object of the present invention to obviate or mitigate at least one of the above-mentioned disadvantages of the prior art.

In one of its aspects, the present invention provides an ultraviolet radiation device comprising a base portion, a plurality of semiconductor structures connected to the base portion and an ultraviolet radiation transparent element connected to the plurality of semiconductor structures.

In one of its aspects, the present invention provides an ultraviolet radiation device comprising a base portion, an ultraviolet radiation transparent element disposed in spaced relation with respect to the base portion and at least one light emitting diode interposed between the base portion and the ultraviolet radiation transparent element; wherein: (i) the at least one light emitting diode is in direct contact with the ultraviolet radiation transparent element, or (ii) there is a spacing between the at least one light emitting diode and the ultraviolet radiation transparent element, the spacing being substantially completely free of air.

In another of its aspects, the present invention provides a fluid treatment system comprising a fluid inlet, a fluid outlet and a fluid treatment zone disposed therebetween, the fluid treatment zone comprising an ultraviolet radiation light emitting diode device, the ultraviolet radiation device comprising an ultraviolet radiation transparent element having a radiation emitting surface configured to be in direct contact with fluid in the fluid treatment zone.

DETAILED DESCRIPTION OF THE PREFERRED EMBODIMENTS

Figure 1:
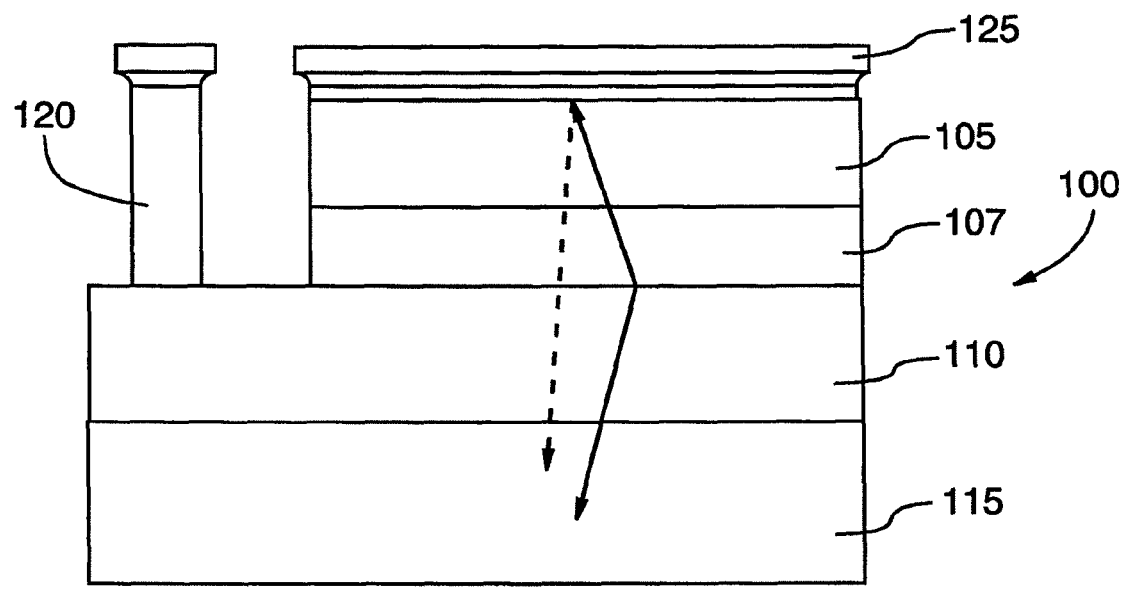
FIG. 1 illustrates the basic structure of an ultraviolet (UV) light emitting diode (LED), according to an embodiment of the present invention.

A schematic for the basic structure of an ultraviolet (UV) light emitting diode (LED) 100 is illustrated in FIG. 1. It consists of layers 105,110 of a semiconductor material that are grown on an insulating substrate 115 that is transparent to emitted ultraviolet radiation. An active layer 107 is interposed between layers 105,110 of the semiconductor material.

The nature of the semiconductor material is not particularly restricted. Non-limiting examples of suitable semiconductor materials include GaN, InN, InGaN, AlInGaN, AlN, AlGaN and mixtures thereof. Throughout this specification, when reference is made to a specific semiconductor material, it is to be understood that this is for illustrative purposes only and should not be used to construe or limit the scope of the invention.

Typically, the insulating substrate may be constructed from sapphire (aluminum oxide). Metallic (or other electrically conductive) contacts are made for the negative (n) terminal 120, and the positive (p) terminal 125. Preferably, part of the semiconductor structure is etched away to contact the n-side of the device, since the substrate is insulating. Using the p-metallic contact 125 as a mirror, the light emitted from the active layer towards the p-side of the device can be reflected back so that it can be emitted out through the transparent substrate 115. The solid arrow in FIG. 1 illustrates the emitted UV light whereas the dashed arrow illustrates the reflected UV light.

Figure 2:
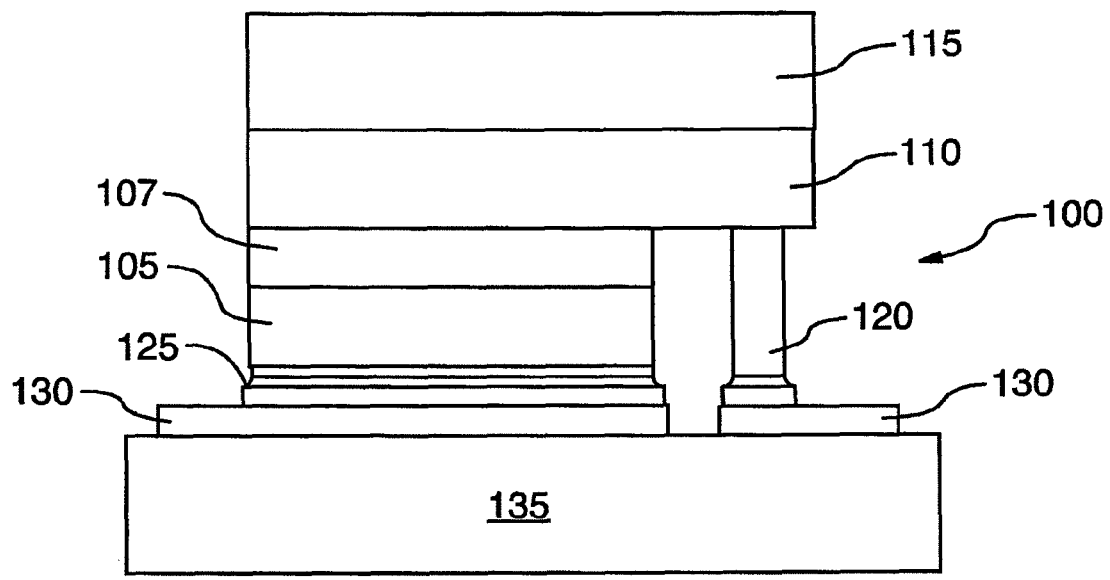
FIG. 2 shows an example of a "flip chip" contacting system, according to an embodiment of the present invention.

In order to make electrical contact without blocking a portion of the emitted radiation produced by UV LED 100, it is preferred to use a "flip chip" contacting system —an example of such a system is shown in FIG. 2, where solder connections (not shown) provide electrical contacts from n metal contact 120 and p metal contact 125 to a printed circuit board 130 mounted on a supporting sub mount 135.

This mounting system allows the UV radiation created by the LED to be emitted in an upwards direction through the substrate while concurrently allowing for electrical contacts.

Figure 3:
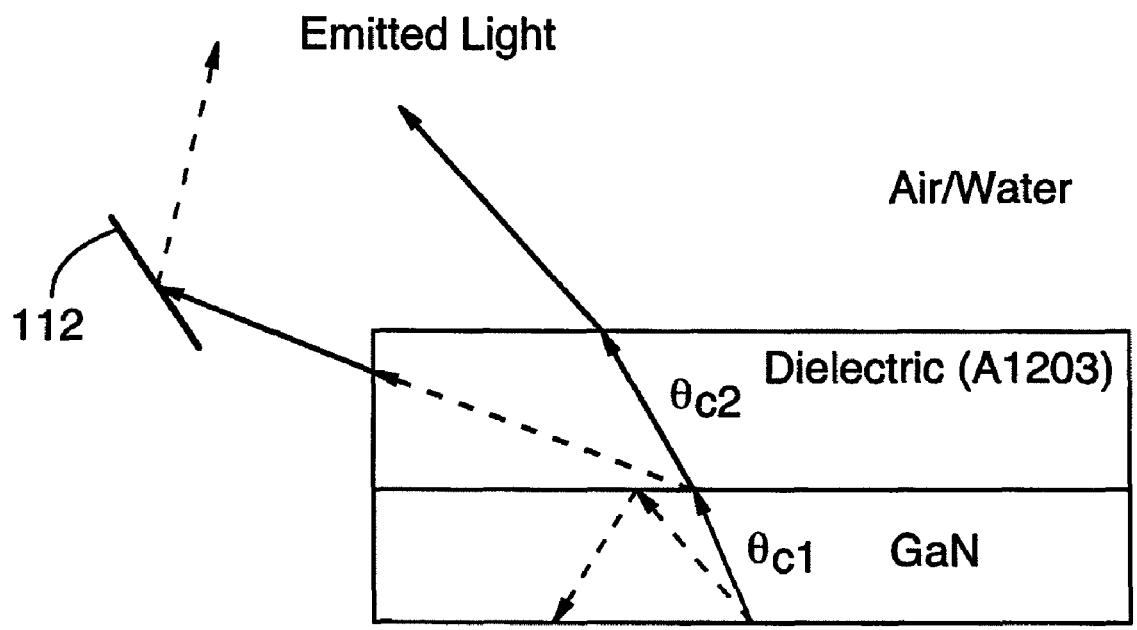
FIG. 3 is a schematic showing how the UV LED can be approximated as a three layer system, according to an embodiment of the present invention.

In order for the device to perform at optimum efficiency, it is preferred that the active layer of the device create the UV light efficiently and that the radiation also escape the device through substrate 115. Since the refractive indices of the materials in the device are different, Snell's law applies and the maximum angle from the vertical $\theta_c$ where light can be emitted is expressed as $$\theta_c = \sin^{-1}(n_1/n_2) \quad [1]$$

for substances with indices of refraction $n_1$ and $n_2$. At angles greater than $\theta_c$, the light is trapped in the first layer by total internal reflection. In FIG. 3, the UV LED can be approximated as a three layer system, where the index of refraction of the UV LED may be assumed to be the index of refraction of the semiconductor material in the UV LED.

If the critical angle is rotated about a line in the vertical direction, an escape cone is defined where all radiation inside the cone can escape into the upper layer. For the UV LED, radiation can be lost outside the escape cone defined by $\theta_{c1}$ and $\theta_{c2}$, although the radiation internally reflecting inside the sapphire substrate (angles $>\theta_{c2}$) can escape through the sides of the substrate provided the radiation is then directed upwards by an external mirror 112 through the window of the LED.

The extraction efficiency $\eta$ of a LED is determined by the equation $$\eta = R \times [1-(1-(n_1/n_2)^2)^{1/2}]/2 \times \Sigma C, \quad [2]$$

where R is the transmission across the interface which accounts for reflection loss, the central expression is the fractional solid angle formed by the escape cone, and the last expression accounts for the number of escape cones.

The solid angle ($\Omega$) of the outer surface of a cone with radius R from the cone tip to the outer surface and angle $\theta$ from the line at the cone center to the edge of the cone is $$\Omega = \text{area of cone surface}/R^2 = 2\pi(1-\cos\theta)$$

The fractional solid angle over $4\pi$ steradians in a sphere is therefore $(1-\cos\theta)/2$. From Equation 1 above, the cone formed by the critical angle has $\sin\theta_c = n_1/n_2$. Using Pythagorean Theorem, $\cos\theta_c = (1-(n_1/n_2)^2)^{1/2}$. Substituting this expression into the fractional solid angle yields $$[1-(1-(n_1/n_2)^2)^{1/2}]/2$$

which appears in Equation 2 above. For the fractional solid angle emitted from the sapphire substrate to the air or water, the maximum solid angle will be a half-sphere or $2\pi$ steradians. The fractional efficiency will therefore be $[1-(1-(n_1/n_2)^2)^{1/2}]$.

For a UV LED, the semiconductor material layer and substrate layer are optically thin, so multiple reflections are possible and the transmission value of R is ~1. Also, there are 2 cones since the LED can emit light from the active layer emitting directly downwards from the substrate, or from light reflected from the p contact metal so $\Sigma C=2$. Equation 2 then reduces to $$\eta \sim [1-(1-(n_1/n_2)^2)^{1/2}]. \quad [3]$$

It should be noted that this is also the same formula for the extraction efficiency from the sapphire layer to air or water if the internally reflected light in the sapphire cannot be collected, since the fractional efficiency is multiplied by 2 since the emission is into a hemisphere, and there is only one cone.

Figure 4:
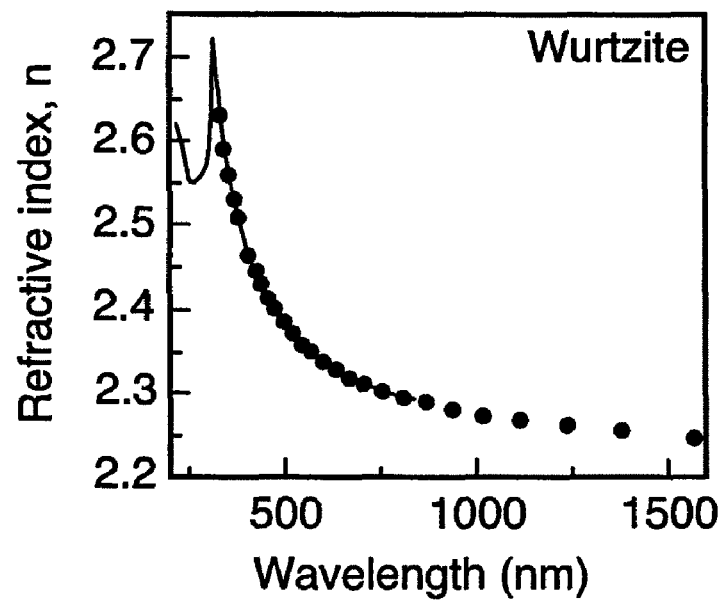
FIG. 4 shows the refractive index of GaN as a function of wavelength (Wurtzite structure-stable alloy).

By way of example, the refractive index of GaN as a function of wavelength (Wurtzite structure-stable alloy) is shown in FIG. 4.

From FIG. 4, it can be seen that the refractive index at 250 nm is ~2.55. Considering a range of dielectric insulating materials, the Melles Griot refractive index data for synthetic quartz gives the refractive index of $SiO_2$ at 250 nm as 1.51. However, the refractive index of deposited $SiO_2$ can vary between 1.46 (standard value) to 1.51 at 450 nm depending on the deposition technique. The 250 nm index of deposited material would therefore be ~1.51-1.56. For silicon nitride ($Si_3N_4$), the index of refraction is 2.0-2.01. Silicon oxynitride ($SiON_x$) compounds will have intermediate indices of refraction at about 1.8 at 250 nm, but the transparency of the material in the UV will need to be determined. The final dielectric material is sapphire with a refractive index of ~1.8 at 250 nm. For the final air or water layer, the refractive index of water at 250 nm is ~1.39 and air is 1.00.

Table 1 shows calculated values of the critical angles for the interfaces listed, as well as the calculated fractional solid angles at these same interfaces. The fractional efficiency can then be calculated for the entire three layer structure, where this value was set to the fractional solid angle of the GaN/dielectric interface if $\theta_{c2}$ is >45° (coded italics in the table). In this case, the escape cone for the top and the sides overlap and all the photons can escape through the interface. If $\theta_{c2}$ is <45° (coded underscored in the table), then the fractional solid angle of the two interfaces are multiplied together to give the fractional efficiency. These calculations were performed for either sapphire or $SiO_2$ dielectrics; and air, water or epoxy upper layers. For a UV LED, a conventional epoxy cannot be used as an upper layer since epoxy may not be transparent to short wavelength light, and will degrade upon prolonged exposure to this light. Thus, the calculations with epoxy were included to compare results with a standard visible LED.

Table 1 illustrates that, for a GaN LED with a sapphire substrate, a 29% efficiency is expected for a visible LED using an epoxy coating. The present inventors have determined that, for a UV LED with a sapphire substrate, the same efficiency can be expected for the device where the upper layer is water, but is only 4.9% when the device is in air. It can be seen that there is a large advantage to be gained in efficiency if the upper layer in the structure is water. Thus, an aspect of the present invention relates to the provision of a UV LED in which the outer sapphire (or other ultraviolet radiation transparent surface) is in direct contact with water—i.e., elimination of the air gap between the layered LED structure and the water layer being treated.

Figure 5:
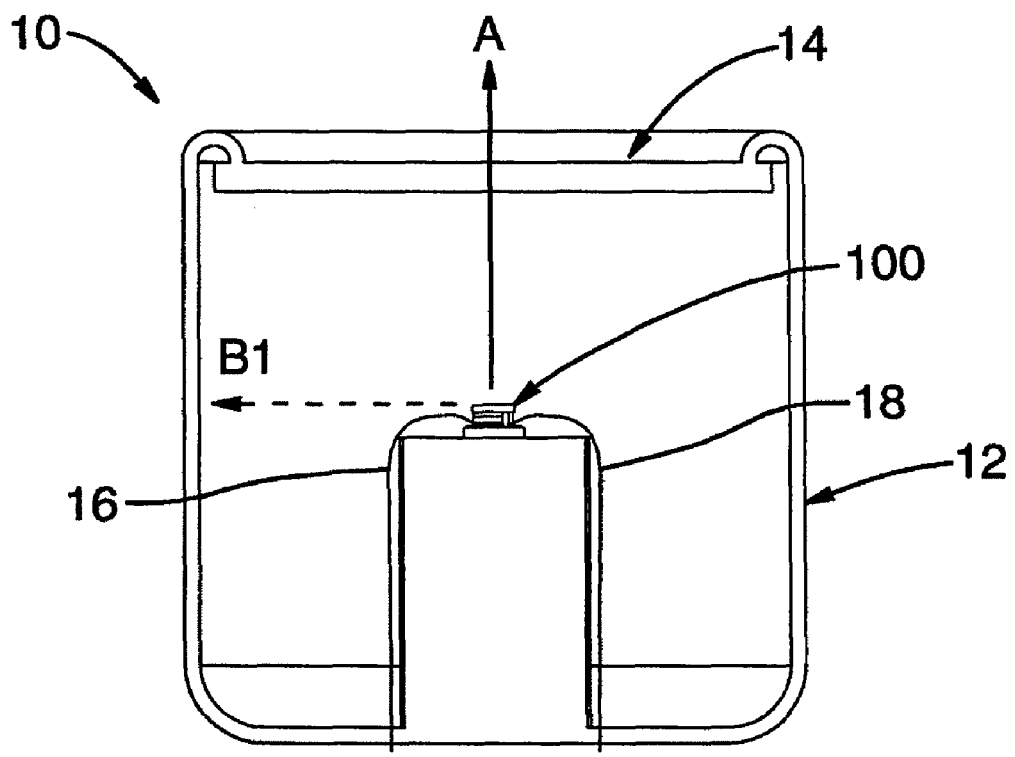
FIG. 5 illustrates a basic device package for a UV light emitting diode device.

A conventional UV light emitting diode device 10 is illustrated in FIG. 5. UV light emitting diode device 10 comprises a metal "can" or container 12 that is used to contain LED 100 described above and a transparent window 14 such as sapphire or quartz is used to allow the UV light to exit the device—Arrow A. Electrical terminals 16,18 are used to supply power to the LED chip. A conventional epoxy encapsulant cannot be used around the LED chip, since it is susceptible to degradation over time with prolonged exposure to UV light. The fundamental problem with this device package is the fact that the light that is internally reflected (Arrow B1) in the sapphire substrate will likely be lost, since most will not be reflected from the inner walls of the device package. This will limit the efficiency of the device to ~5% according to the calculations shown in Table 1, since the device has a sapphire/air interface. Additionally, since the sub mount of the LED 100 is attached to the bottom of the metal container, the heat generated by the device is significant. This build up of heat near the chip will shorten its lifespan.

Figure 6:
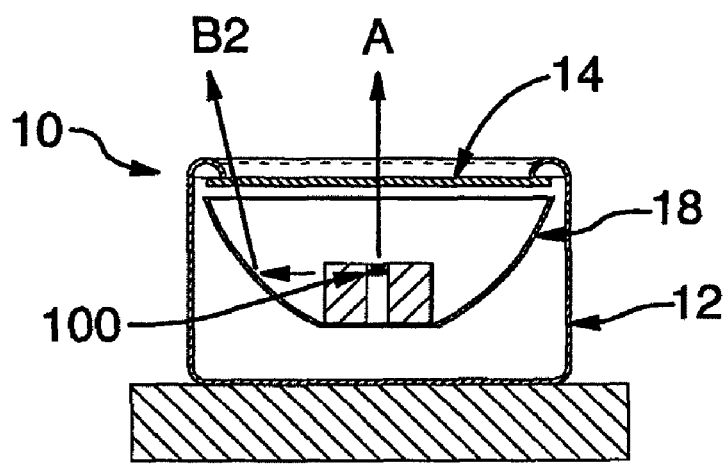
FIG. 6 illustrates a packaged UV LED with a reflector.

The prior art has taught that improvement can be made to the basic design by incorporating a light reflecting assembly 18 around the LED chip as shown in FIG. 6. The light emitted from the side of the substrate is then re-directed upwards through the transparent window—arrow B2.

There are a number of disadvantages for a UV LED made using this prior art approach.

First, a specially machined miniature reflector that effectively reflects UV light will be costly to produce. It is well known in the semiconductor industry that packaging costs are a major part of the total cost of the device and the need for a miniature reflector will significantly increase this cost. Thus, an alternate method of collecting the light outside of the escape cone of the sapphire substrate would be highly desirable.

Second, the principal manner by which heat may escape the device is downwards through the sub mount and bottom of the device container. A design for an LED that would allow an additional path for heat to be removed from the device would be very advantageous.

Finally, a device that can offer greater disinfection power density in UV watts would allow for higher flow rates of water to be disinfected. The actual device shown in FIG. 6 produces only 1 mW of 280 nm UV light.

Figure 7A:
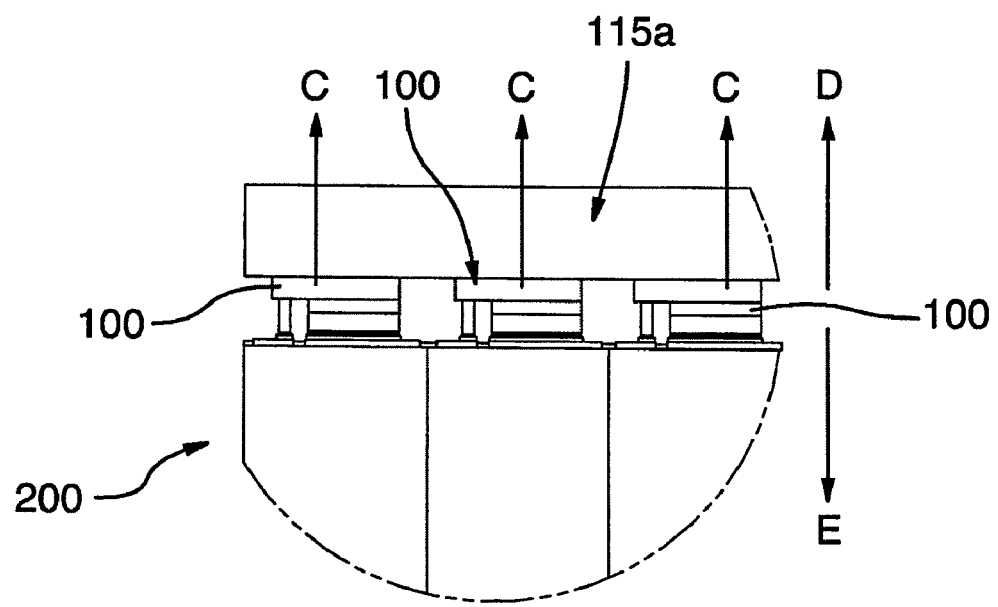
FIG. 7a is a schematic of a direct contact UV LED array device, which comprises a series of LEDs.

As described above, the escape cone from sapphire to water is much larger than the escape cone to air, with a 29% versus 4.5% fractional efficiency assuming all the light can escape to the water from sapphire with a >45° escape cone angle. A device which has the sapphire substrate in direct contact with the water to be disinfected would also provide an additional path for heat to escape the LED. A schematic of a direct contact UV LED array device 200 is shown in FIG. 7a which comprises a series of LED 100 as described above with the modification of using a single top layer of the sapphire substrate 115a instead of individual sapphire substrates 115 for each LED 100. As shown, top layer sapphire substrate 115a is configured to be in direct contact with the water. Most of the light is coupled upwards (Arrow C) through the escape cone, so the light emitted from the side of the substrate can be neglected.

The output of many UV LEDs 100 are available using UV LED array device 200, so that a higher total UV output power is achieved. The provision of many UV LEDs 100 will result in the production of a significant amount of heat. An advantage of UV LED array device 200, is that this excess heat may be efficiently dissipated by virtue of heat transfer via two separate pathways: heat transfer to the fluid (Arrow D) (e.g., a liquid such as water, although other liquids and gaseous fluids may be used in the context of the invention) and heat transfer to the bottom of the device (Arrow E). An additional feature of this device is that the provision of a substantially flat outer surface for sapphire substrate 115a facilitates cleaning thereof to removing fouling materials that may accumulate thereon at the surface fluid interface. More specifically, the substantially flat outer surface for sapphire substrate 115a will easily allow a wiping mechanism (chemical, mechanical or combined chemical/mechanical) to pass over the surface to remove fouling materials that would otherwise reduce the UV output of UV LED array device.

In FIG. 7a, the positive and negative terminals of the individual UV LEDs 100 are connected together via printed circuit paths (not shown for clarity) to supply power to all UV LEDs 100.

Figure 7B:
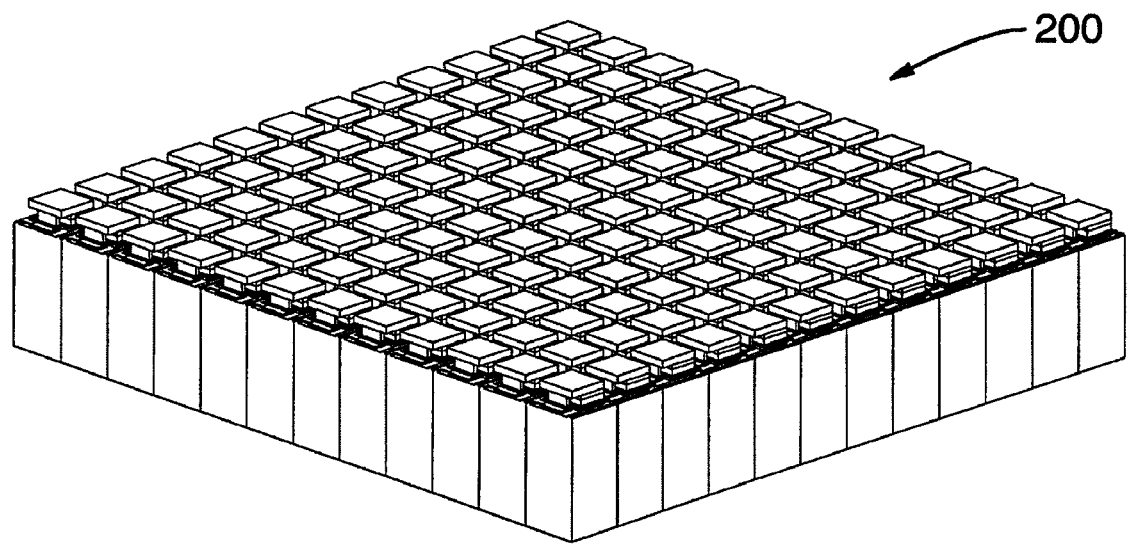
FIG. 7b illustrates a perspective view of UV LED array device with sapphire substrate removed for clarity.

FIG. 7b illustrates a perspective view of UV LED array device 200 with sapphire substrate 115a removed for clarity.

Figure 7C:
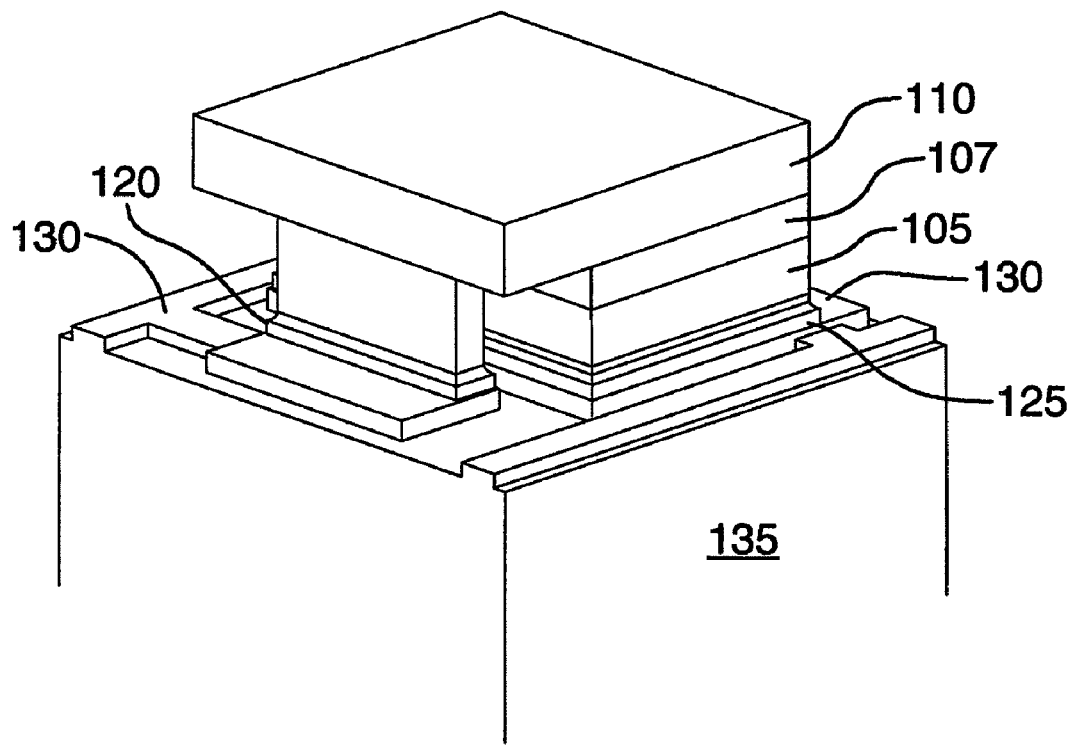
FIG. 7c illustrates an enlarged isometric view of a single LED device in the UV LED array device illustrated in FIG. 7b (with sapphire substrate removed for clarity).

FIG. 7c illustrates an enlarged isometric view of a single LED device in UV LED array device 200 illustrated in FIG. 7b (with sapphire substrate 115a removed for clarity).

The UV LED array can be manufactured by a semiconductor processing method. Initially, the AlGaN semiconductor (or other semiconductor) layers are deposited on a continuous sapphire substrate. Next, portions of the AlGaN layers are etched down all the way to the sapphire substrate to create an array of semiconductor structures comprising the AlGaN semiconductor (or other semiconductor) layers. The semiconductor structures created by this process are physically separated from one another but still bonded to a continuous sapphire substrate which will act as the radiation emitting window for the entire array. Metallic contacts are then formed on the appropriate layers and, if desired, large areas are then separated into individual arrays. A sub mount which contacts all the p and n contacts of the individual chips is then attached to the chips for a multi "flip-chip" design.

A possible modification to direct contact UV LED array device shown in FIG. 7a is to include a quartz or other UV transparent window that is in contact with the sapphire substrate (not shown for clarity). This would reinforce the sapphire substrate and still allow UV light to pass through into the water.

Figure 8A:
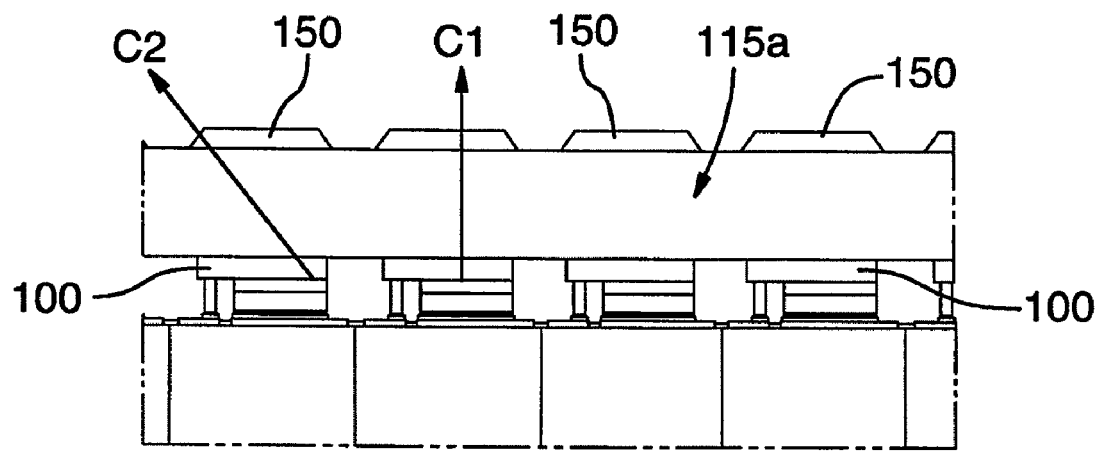
FIG. 8a shows how the surface of the sapphire substrate could be modified to include a series of sapphire dome elements.

In the event that there is still an appreciable amount of light that is trapped within the sapphire substrate due to total internal reflection, the surface of the sapphire substrate could be modified as shown in FIG. 8a to include a series of sapphire dome elements 150. As shown, each sapphire dome element 150 is disposed in general alignment with LED device 100. Light within the escape cone can exit the sapphire substrate in the flat region directly above the LED chip (Arrow C1), while light that is normally outside the escape cone (Arrow C2) exits the substrate through the angled portion so that the exit angle is less than the critical angle for a sapphire/water interface.

Figure 8B:
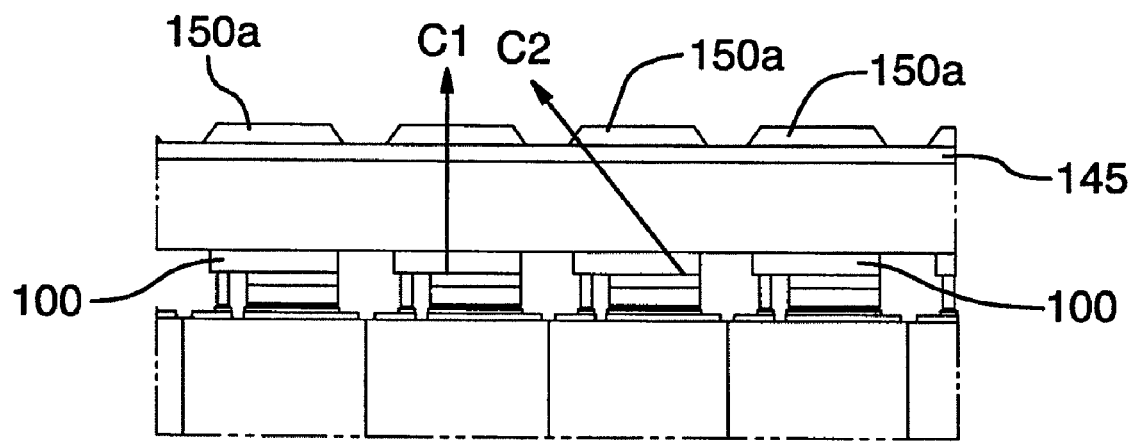
FIG. 8b shows how the modification to the surface could also be present in a top quartz layer in contact with sapphire layer.

The modification to the surface could also be present in a top quartz layer 145 in contact with sapphire layer 115a as shown in FIG. 8b. Top quartz layer 145 comprises a series of quartz dome elements 150a. As shown, each dome element 150a is disposed in general alignment with LED device 100. The index of refraction difference between sapphire and quartz will be minimal so the amount of refraction at this interface is small. Thus, light can exit the device via Arrow C1 and/or Arrow C2 as described above.

The improvements in efficiency, heat extraction and cleaning associated with the present ultraviolet radiation device have been mentioned above.

A further improvement to the total possible power density also accrues from the present ultraviolet radiation device. Zhang et al. teach that processing of a conventional UV LED yields 1 mW power for a chip with an area of $2\times10^{-4}$ cm$^2$. Thus, 50% coverage of a 1 cm$^2$ area would give an array with 2,500 LED chips. At 1 mW power each, the UV LED array would have a power of 2.5 W and power density of 2.5 W/cm$^2$. This compares favorably with the power densities of mercury lamps, and does not assume any increase in the electrical efficiency of the electrical device beyond the original 0.85%. Improvements in efficiency using the features of this invention will increase the power density. Practically, the total power consumption of such an array would be ~6V×0.12 A/chip [6]×2,500 chips=300 W. This would be a large amount of heat to extract for a 1 cm$^2$ area, so reduction of the chip density to 5% would give a total UV power of 250 mW (250 mW/cm$^2$ power density) and a power consumption of 30 W.

Extraction of heat resulting from 30 W is reasonably achievable, and the power density of 250 mW/cm$^2$ still compares favorably to that of low pressure mercury lamps. It is believed that improvements in efficiency will increase the UV output at a constant power consumption of 30 W. The embodiment of the present ultraviolet radiation device in the form of an array could be put into practice using a number of discrete UV LEDs with the substrate window or the substrate/quartz window in contact with the water to give increased light coupling efficiency and heat extraction, but the array embodiment would be preferred to maximize the UV power density.

The present ultraviolet radiation device may be used in a fluid treatment system that capitalizes on the higher UV power densities possible with UV LED arrays and the more efficient heat extraction possible with the present ultraviolet radiation device. Also, it is believed that the efficiency of this array should be better than that of a system using discrete LEDs in a container, since a direct contact between the light emitting surface of the LED and the fluid (e.g., water) exists.

Figure 9:
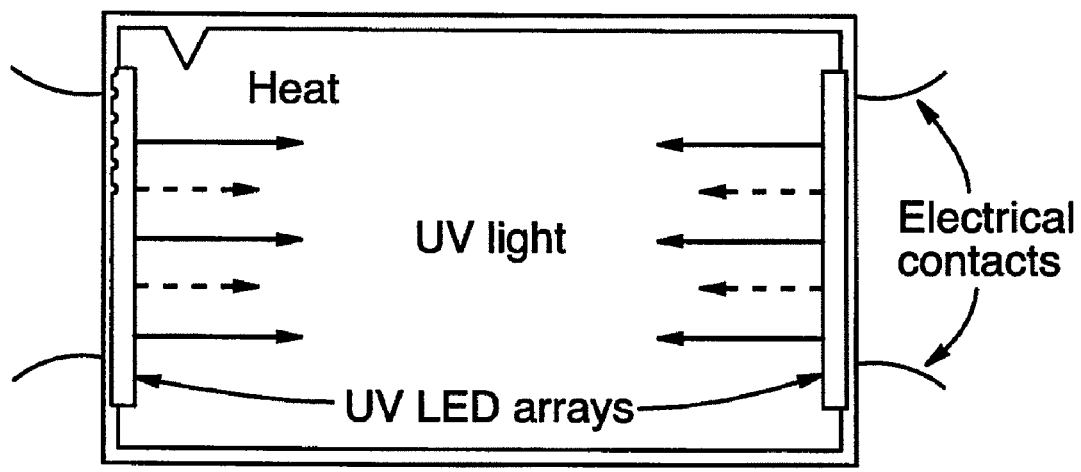
FIG. 9 illustrates a schematic of a UV LED Reactor, in cross-section.

FIG. 9 illustrates a schematic of such a reactor. UV LED arrays 200 are preferably mounted on a thermally conductive metal surface which is also in contact with the fluid (e.g., water) to be treated. Thus, heat generated during operation of the LED array can be extracted by the fluid (e.g., water), either directly through the radiation transparent substrate/window of the LED array or via the metal enclosure of the reactor which acts as a heat sink—this is illustrated with hashed arrows whereas the solid arrows depict UV radiation transmission. The LED arrays will be capable of higher UV output powers than discrete LEDs (FIG. 5 or 6), so that larger volumes of water may be treated in the reactor (i.e., higher throughput). Electrical power is supplied by wires through the metal enclosure, and a wiping system that passes over the surface of the LED arrays to reduce fouling can be installed.

All publications, patents and patent applications referred to herein are incorporated by reference in their entirety to the same extent as if each individual publication, patent or patent application was specifically and individually indicated to be incorporated by reference in its entirety.

TABLE 1

Calculated Critical Angles, Fractional Solid Angles and Fractional Efficiencies for UV LED Materials Systems

| Substance 1 | Substance 2 | n1 | n2 | Critical Angle (°) | Fractional Solid Angle |
|---|---|---|---|---|---|
| SiO$_2$ | GaN | 1.51 | 2.55 | 36.31 | 0.194 |
| water | SiO$_2$ | 1.39 | 1.51 | 67.00 | 0.609 |
| air | SiO$_2$ | 1 | 1.51 | 41.47 | 0.251 |
| epoxy | SiO$_2$ | 1.5 | 1.51 | 83.40 | 0.885 |

| Substance 1 | Substance 2 | n1 | n2 | Critical Angle (°) | Fractional Efficiency |
|---|---|---|---|---|---|
| GaN/SiO$_2$/water | | | | | 0.194 |
| GaN/SiO$_2$/air | | | | | 0.049 |
| GaN/SiO$_2$/epoxy | | | | | 0.194 |

| Substance 1 | Substance 2 | n1 | n2 | Critical Angle (°) | Fractional Solid Angle |
|---|---|---|---|---|---|
| SiON$_x$/Al$_2$O$_3$ | GaN | 1.8 | 2.55 | 44.90 | 0.292 |
| water | SiON$_x$/Al$_2$O$_3$ | 1.39 | 1.8 | 50.55 | 0.365 |
| air | SiON$_x$/Al$_2$O$_3$ | 1 | 1.8 | 33.75 | 0.169 |
| epoxy | SiON$_x$/Al$_2$O$_3$ | 1.5 | 1.8 | 56.44 | 0.447 |

Critical

TABLE 1-continued

Calculated Critical Angles, Fractional Solid Angles and
Fractional Efficiencies for UV LED Materials Systems

| Substance 1 | Substance 2 | n1 | n2 | Angle (°) | Fractional Efficiency |
|---|---|---|---|---|---|
| GaN/Al$_2$O$_3$/water | | | | | 0.292 |
| GaN/Al$_2$O$_3$/air | | | | | 0.049 |
| GaN/Al$_2$O$_3$/epoxy | | | | | 0.292 |

What is claimed is:

1. A water treatment ultraviolet radiation device comprising:
a base portion;
a plurality of semiconductor structures connected to the base portion, each semiconductor structure including a reflector configured to direct UV radiation away from said base, each semiconductor structure also including a first semiconductor layer, an active layer, a second semiconductor layer, and a substrate configured to pass the UV radiation therethrough; and
a single, substantially flat, dielectric substrate, ultraviolet radiation transparent element in direct contact with each substrate of the plurality of semiconductor structures, said single, substantially flat, dielectric substrate comprising sapphire and being in direct contact with the water to be treated such that there are no air gaps between (i) each substrate of the plurality of semiconductor structures and (ii) said water to be treated.

2. The water treatment ultraviolet radiation device defined in claim 1, wherein an escape cone of sapphire to water is large enough to produce substantially 29 percent fractional efficiency.

3. The water treatment ultraviolet radiation device defined in claim 1, wherein each semiconductor structure comprises a semiconductor material.

4. The water treatment ultraviolet radiation device defined in claim 1, wherein each semiconductor structure comprises a member selected from the group comprising GaN, InN, InGaN, AlInGaN, AlN, AlGaN and mixtures thereof.

5. The water treatment ultraviolet radiation device defined in claim 1, wherein each semiconductor structure first layer comprises a first semiconductor material and each second layer comprises a second semiconductor material.

6. The water treatment ultraviolet radiation device defined in claim 5, wherein the first layer is electrically connected to the base portion by a first contact element.

7. The water treatment ultraviolet radiation device defined in claim 5, wherein the second layer is electrically connected to the base portion by a second contact element.

8. The water treatment ultraviolet radiation device defined in claim 5, wherein the first layer is electrically connected to the base portion by a first contact element and the second layer is electrically connected to the base portion by a second contact element.

9. The water treatment ultraviolet radiation device defined in claim 5, wherein the first semiconductor material and the second semiconductor material are independently selected from the group comprising GaN, InN, InGaN, AlInGaN, MN, AlGaN and mixtures thereof.

10. The water treatment ultraviolet radiation device defined in claim 1, wherein said plurality of semiconductor substrates provides at least substantially 250 mW/cm$^2$ power density.

11. The water treatment ultraviolet radiation device defined in claim 1, wherein said plurality of semiconductor substrates provides a chip density of substantially 5 percent.

12. The water treatment ultraviolet radiation device defined in claim 1, wherein said plurality of semiconductor substrates has a power consumption of not greater than substantially 30 W.

13. The water treatment ultraviolet radiation device defined in claim 1, wherein the ultraviolet radiation transparent element comprises a laminate structure.

14. The water treatment ultraviolet radiation device defined in claim 13, wherein the laminate structure comprises a first layer and a second layer.

15. The water treatment ultraviolet radiation device defined in claim 13, wherein the first layer and the second layer comprise the same material.

16. The water treatment ultraviolet radiation device defined in claim 13, wherein the first layer and the second layer comprise different materials.

17. The water treatment ultraviolet radiation device defined in claim 13, wherein one of the first layer and the second layer comprises quartz.

18. The water treatment ultraviolet radiation device defined in claim 13, wherein both of the first layer and the second layer comprise sapphire.

19. The water treatment ultraviolet radiation device defined in claim 13, wherein the first layer comprises quartz and the second layer comprises sapphire.

20. The water treatment ultraviolet radiation device defined in claim 1, wherein ultraviolet radiation transparent element comprises a substantially planar surface.

21. The water treatment ultraviolet radiation device defined in claim 1, wherein the ultraviolet radiation is sapphire.

22. The water treatment ultraviolet radiation device defined in claim 1, wherein the base comprises a thermally-conductive material.

23. The water treatment ultraviolet radiation device defined in claim 1, wherein said ultraviolet radiation transparent element comprises a thermally-conductive material.

24. The water treatment ultraviolet radiation device defined in claim 1, further comprising, for each said semiconductor structure, a projection disposed on an outer surface of said ultraviolet radiation transparent element in substantial alignment with said each semiconductor structure substrate.

25. The water treatment ultraviolet radiation device defined in claim 24, wherein each projection has a cross-sectional shape in the form of a dome.

26. A water treatment ultraviolet radiation device comprising:
a base portion;
a plurality of UV LEDs coupled to the base portion, each LED including a reflector configured to direct UV radiation away from said base, each LED comprising a first semiconductor layer, an active layer, a second semiconductor layer, and a substrate configured to pass the UV radiation therethrough;
a single, substantially flat, dielectric substrate, ultraviolet radiation transparent element in direct contact with each substrate of the plurality of LEDs, said single, substantially flat, dielectric substrate comprising a layer including sapphire and a layer including quartz, said layer including quartz being in direct contact with the water to be treated such that there are no air gaps between (i) each substrate of the plurality LEDs and (ii) said water to be treated.

27. The water treatment ultraviolet radiation device defined in claim 26, wherein an escape cone of sapphire to water is large enough to produce substantially 29 percent fractional efficiency.

28. The water treatment ultraviolet radiation device defined in claim 26, wherein each LED comprises a dielectric substrate.

29. The water treatment ultraviolet radiation device defined in claim 26, wherein at least one semiconductor layer comprises a member selected from the group comprising GaN, InN, InGaN, AlInGaN, AlN, AlGaN and mixtures thereof.

30. The water treatment ultraviolet radiation device defined in claim 26, wherein each LED comprises a dielectric substrate and a thermally conductive base.

31. The water treatment ultraviolet radiation device defined in claim 30, wherein each semiconductor layer comprises a member selected from the group comprising GaN, InN, InGaN, AlInGaN, AlN, AlGaN and mixtures thereof.

32. The water treatment ultraviolet radiation device defined in claim 26, wherein the ultraviolet radiation transparent element comprises $Al_2O_3$.

33. The water treatment ultraviolet radiation device defined in claim 26, wherein the base portion is disposed in a housing.

34. The water treatment ultraviolet radiation device defined in claim 33, wherein the housing comprises a pair of side walls and a base wall, the base portion of the LED being connected to the base wall of the housing.

35. The water treatment ultraviolet radiation device defined in claim 33, wherein the ultraviolet radiation transparent element is connected to the housing opposite the base wall.

36. The water treatment ultraviolet radiation device defined in claim 33, wherein the housing further comprises the reflector which is configured to reflect the UV radiation emitted from the LED through the ultraviolet radiation transparent element.

37. A fluid treatment system comprising:
 a fluid inlet, a fluid outlet, and a fluid treatment zone disposed therebetween,
 the fluid treatment zone comprising a water treatment ultraviolet radiation device defined in claim 26, wherein the layer including quartz is in direct contact with the water in the fluid treatment zone.

38. The fluid treatment system defined in claim 37, wherein the ultraviolet radiation device is connected to a wall of the fluid treatment zone.

39. The fluid treatment system defined in claim 37, wherein the ultraviolet radiation transparent element comprises a surface of the fluid treatment zone.

40. The fluid treatment system defined in claim 37, further comprising another water treatment ultraviolet radiation device defined in claim 1.

41. The fluid treatment system defined in claim 40, wherein the water treatment ultraviolet radiation device and the another water treatment ultraviolet radiation device are disposed opposite one another in the fluid treatment zone.

42. The fluid treatment system defined in claim 37, wherein the fluid treatment zone has an open cross-section.

43. The fluid treatment system defined in claim 37, wherein the fluid treatment zone has a closed cross-section.

44. The fluid treatment system defined in claim 37, wherein the fluid inlet is adapted to receive the water to be treated.

45. The fluid treatment system defined in claim 37, wherein the ultraviolet radiation transparent element is configured to transfer heat to the water to be treated.

46. The fluid treatment system defined in claim 37, wherein the fluid inlet is adapted to receive the water to be treated, which includes one or more fluids selected from the group comprising milk, whey, oil, bodily fluid, and mixtures thereof.

47. The ultraviolet radiation device defined in claim 1, further comprising a cleaning element for removing fouling materials from at least a portion of the ultraviolet radiation transparent element exposed to the water to be treated.

48. A water treatment ultraviolet radiation device comprising:
 a base portion;
 a plurality of semiconductor structures connected to the base portion, each semiconductor structure including a reflector configured to direct UV radiation away from said base, each semiconductor structure also including a first semiconductor layer, an active layer, a second semiconductor layer, and a substrate configured to pass the UV radiation therethrough;
 a single, substantially flat, dielectric substrate, ultraviolet radiation transparent element in direct contact with each substrate of the plurality of semiconductor structures, said single, substantially flat, dielectric substrate comprising sapphire; and
 a single quartz layer having one surface in direct contact with said single, substantially flat, dielectric substrate, ultraviolet radiation transparent element, and being in direct contact with the water to be treated such that there are no air gaps between (i) each substrate of the plurality of semiconductor structures and (ii) said water to be treated.

49. The water treatment ultraviolet radiation device defined in claim 48, wherein an escape cone of sapphire to water is large enough to produce substantially 29 percent fractional efficiency.

50. The water treatment ultraviolet radiation device defined in claim 48, wherein said plurality of semiconductor substrates provides at least substantially 250 $mW/cm^2$ power density.

51. The water treatment ultraviolet radiation device defined in claim 48, wherein said plurality of semiconductor substrates provides a chip density of substantially 5 percent.

52. The water treatment ultraviolet radiation device defined in claim 48, wherein said plurality of semiconductor substrates has a power consumption of not greater than substantially 30 W.

53. The water treatment ultraviolet radiation device defined in claim 48, further comprising, for each said semiconductor structure, a projection disposed on an outer surface of said ultraviolet radiation transparent element in substantial alignment with said each semiconductor structure substrate.

* * * * *